United States Patent [19]

Dietl et al.

[11] 4,360,469

[45] Nov. 23, 1982

[54] PREPARATION OF QUINONES BY SALCOMINE-CATALYZED OXIDATION OF PHENOLS

[75] Inventors: Hans K. Dietl; Howard S. Young, both of Kingsport, Tenn.

[73] Assignee: Eastman Kodak Company, Rochester, N.Y.

[21] Appl. No.: 45,536

[22] Filed: Jun. 11, 1970

[51] Int. Cl.$^3$ .................. C07C 50/04; C07C 50/08; C07C 50/12; C07C 50/24; C07C 50/28; C07C 76/02

[52] U.S. Cl. .................. 260/396 R; 260/396 N; 568/652; 568/711; 568/737; 568/747; 568/765; 568/772; 568/746

[58] Field of Search .......... 260/396 R, 396 K, 396 N

[56] References Cited

U.S. PATENT DOCUMENTS 3,455,880  7/1969  Kobayashi et al. ............. 260/396 R
3,658,852  4/1972  Schuster et al. ................ 260/396 R

*Primary Examiner*—Vivian Garner
*Attorney, Agent, or Firm*—J. Frederick Thomsen; Daniel B. Reece, III

[57] ABSTRACT

It has been found that unexpectedly high yields of a high purity product can be obtained when substituted p-quinones are prepared by oxidation, using a molecular oxygen-containing gas, of the corresponding phenols in an inert solvent having a dipole moment of at least 2.7 and in the presence of a salcomine catalyst.

17 Claims, No Drawings

PREPARATION OF QUINONES BY SALCOMINE-CATALYZED OXIDATION OF PHENOLS

This invention relates to the preparation of substituted p-quinones by the oxidation of substituted phenols in the presence of salcomine as a catalyst. More particularly, the present invention is concerned with an improved oxidation process of this general type.

The oxidation of highly substituted phenols with a molecular oxygen-containing gas to the corresponding substituted p-quinones in methanol or chloroform as the inert solvent using salcomine as a catalyst has been described in the literature (See, for instance, H. M. van Dort and H. J. Geursen, Recueil 86, 520, 1967). However, the yields of substituted p-quinone obtained are moderate, the reaction rate is quite slow, and the catalyst consumption, ease of product recovery and purity of product leave much to be desired. As a consequence, industry has turned to other more economical routes for the manufacture of substituted p-quinones as, for instance, by the oxidation of substituted aniline.

An object of the invention, therefore, is to provide an improved process for oxidizing substituted phenols to the corresponding substituted p-quinones in an inert solvent with a molecular oxygen-containing gas and in the presence of salcomine catalyst which process is not handicapped by the aforementioned drawbacks.

Another object of the invention is to provide a process for the production of high selective yields of substituted p-quinones by the air oxidation of substituted phenols.

A further object of the invention is to provide a process for the oxidation of substituted phenol to substituted p-quinone which can list as additional advantages a high production rate, easy product recovery, low catalyst consumption and a pure product.

These and other objects of the invention are obtained by simply carrying out the oxidation process in an inert organic polar solvent having a dipole moment of at least about 2.7, preferably a dipole moment of above 3.3. Among the polar solvents suitable for use in the present invention may be included dimethylacetamide, dimethylformamide, γ-butyrolactone, sulfolane, N-methylpyrrolidone, acetonitrile, benzonitrile and adiponitrile.

The salcomine catalyst employed in the process of the invention is a cobalt(II) chelate with the Schiff base of ethylene-diamine and salicylaldehyde as the organic ligand. The catalyst may be prepared according to procedures described in the literature as, for instance, H. Diehl and C. C. Hach, Inorg. Synthesis 3, 196, (1950). An alternate and equally suitable general procedure for preparing the catalyst is as follows:

A quantity of 0.1 gram mole of cobaltous chloride, acetate or sulfate is dissolved in 200 ml. water and 0.2 gram mole salicylaldehyde in 200 ml. ethanol is added under stirring. 0.1 gram Mole of diamine in 100 ml. water/ethanol (50:50) then is added under stirring over a period of 10 minutes. Stirring is continued for 30 minutes and the reaction mixture is allowed to stand overnight. The precipitate is filtered out, washed with 1 liter warm water and dried in a vacuum at 80° C.

The phenols oxidized in accordance with the process of the invention should have at least two substituents on the ring in any two or more of the 2,3,5 and 6 positions on the ring. Suitable substituents include, for instance, alkyl groups, aryl groups, alkoxy groups, halogen groups, groups joined together to form condensed rings as in the case of 1-naphthol and any other substituents which do not unduly inhibit the oxidation of the phenol to the corresponding p-quinone. Illustrative of specific phenols which may be used as starting materials are 2,3-dimethylphenol, 2,5-dimethylphenol, 2,6-dimethylphenol, 2,3,5-trimethylphenol, 2,3,6-trimethylphenol, 2,3-diethylphenol, 2,5-dipropylphenol, 2-methyl-5-ethylphenol, 3-hexyl-5-methylphenol, 2,5-dibromophenol, 2,6-dichlorophenol, 2,5-dihydroxyphenol, 2,3,6-trichlorophenol, 2,5-dichloro-3,6-dihydroxyphenol, 2,6-dinitrophenol, 2,3-dinitrophenol, 3,5-dinitrophenol, 2-methoxy-5-ethylphenol, 3-ethoxy-5-methylphenol, 2,6-diphenylphenol, 2-phenyl-5-chlorophenol, 1-naphthol, etc.

Air may be conveniently used as the molecular oxygen-containing gas in the oxidation process, although pure oxygen or gas mixtures containing an oxygen content of more or less than that normally found in air may be employed, if desired. The air or oxygen pressure in the reaction is not critical although a pressure of about 5 to 500 psi. is preferred. The oxidation proceeds readily at ambient temperatures and pressures but elevated temperatures as well as below-room-temperature temperatures can be used. In general, the reaction temperatures employed will fall in the range of about −30° to 80° C. and preferably about 0° to 70° C.

The substituted p-quinone reaction product formed may be isolated from the reaction mixture by simply quenching the reaction mixture with cold water. The quenching effects immediate precipitation of the p-quinone product from the reaction mixture permitting easy recovery by conventional separation techniques such as filtering, decanting, centrifuging and the like. The products can also be recovered directly from the reaction solution, without quenching, by steam distillation.

Exemplary of substituted p-quinones that may be produced by the present invention are 2,3-dimethyl-p-quinone, 2,5-dimethyl-p-quinone, 2,6-dimethyl-p-quinone, 2,3,5-trimethyl-p-quinone, 2,3,6-trimethyl-p-quinone, 2,3-diethyl-p-quinone, 2,5-dipropyl-p-quinone, 2-methyl-5-ethyl-p-quinone, 3-hexyl-5-methyl-p-quinone, 2,5-dibromo-p-quinone, 2,6-dichloro-p-quinone, 2,5-dihydroxy-p-quinone, 2,3,6-trichloro-p-quinone, 2,5-dichloro-3,6-dihydroxy-p-quinone, 2,6-dinitro-p-quinone, 2,3-dinitro-p-quinone, 3,5-dinitro-p-quinone, 2-methoxy-5-ethyl-p-quinone, 3-ethoxy-5-methyl-p-quinone, 2,6-diphenyl-p-quinone, 2-phenyl-5-chloro-p-quinone, etc.

Substituted p-quinones find a variety of uses as, for example, oxidizng agents, the tanning of hides, the strengthening of animal fibers, the manufacture of dyes, etc. The quinones may also be reduced to the corresponding hydroquinones which are valuable developing agents in photography.

The following examples are included to further illustrate the process of the present invention.

EXAMPLE I

80 Grams of 2,6-dimethylphenol in 300 ml. of dimethylformamide is placed in a 500 ml. resin kettle oxidizer provided with air inlet, stirrer, thermometer, and a reflux condenser. 2.5 Grams of salcomine catalyst is added and the contents heated to a temperature of 35° C. Air is then introduced at a rate of 0.30 l./min. and the stirrer is run at a speed of 277 rpm. When the oxidation unit reaches a pressure of 150 psi., venting is commenced to control the pressure. The oxidation is continued until no further 2,6-dimethylphenol remains. 2,6-Dimethylquinone product is isolated in good purity by quenching the reaction solution with cold water, filtering and drying. A yield of 99% of dimethylquinone is obtained.

EXAMPLE II

Example I is repeated substituting dimethylacetamide for the dimethylformamide in the reaction solvent medium. A similar high yield of 2,6-dimethylquinone product is obtained.

EXAMPLE III

Example I is repeated substituting 2-butanone for dimethylformamide. A 72% yield of 2,6-dimethylquinone is obtained.

EXAMPLE IV

Example I is repeated substituting methanol for dimethylformamide in the reaction solvent medium. Red crystals of the corresponding diphenoquinone are formed. Yield of the diphenoquinone is 30%. The diphenoquinone is filtered off and the filtrate is quenched with water. 2,6-Dimethylquinone is filtered off and dried. The yield is only 65%.

EXAMPLE V

40 Grams of 2,3,6-trimethylphenol in 200 ml. dimethylformamide is oxidized as described in Example I. 2,3,6-Trimethyl-p-quinone is isolated as pure material by steam distilling the reaction solution and extracting the steam distillate with a water immiscible organic solvent. A yield of 95% of 2,3,6-trimethyl-p-quinone is obtained.

EXAMPLE VI

Example V is repeated substituting γ-butyrolactone for dimethylformamide as a reaction solvent medium. Similar high yields of pure trimethylquinone are obtained.

EXAMPLE VII

Example V is repeated substituting 2,3,5-trimethylphenol for the 2,3,6-trimethylphenol. A yield of 85% of 2,3,5-trimethyl-p-quinone is obtained.

EXAMPLE VIII

50 Grams 2,3,6-trimethylphenol in 200 ml. dimethylformamide is oxidized as in Example I except the temperature is raised to 55° C. and the pressure is 100 psi. The product is recovered by steam distillation as in Example 5. The yield is 93% 2,3,6-trimethyl-p-quinone.

EXAMPLE IX

Example VIII is repeated except reaction conditions are room temperature and at atmospheric pressure. The yield is 92%, 2,3,6-trimethyl-p-quinone.

EXAMPLE X 2,3,6-Trimethylphenol and dimethylformamide are combined so as to produce a weight ratio of phenol to solvent of 0.2. Reaction conditions are 40° C., 200 psi.; recovery is through steam distillation, and the yield of 2,3,6-trimethyl-p-quinone is 92%.

EXAMPLE XI

Example X is repeated except the weight ratio of phenol to solvent is 1.0. The yield of 2,3,6-trimethyl-p-quinone is 77%.

Although the invention has been described in considerable detail with reference to certain preferred embodiments thereof, it will be understood that variations and modifications can be effected within the spirit and scope of the invention.

We claim:

1. In the preparation of substituted p-quinones wherein the p-quinone has at least two substituents on the ring in any two or more of the two, three, five and six positions said substituents selected from the group consisting of alkyl of from 1 to 6 carbon atoms, alkoxy, halogens, hydroxy, nitro, phenyl, and the radical—CH=CH—CH=CH—which joins the quinoid ring to form a naphthoquinone ring, by the oxidation of similarly substituted phenols in an inert solvent with a molecular oxygen-containing gas and in the presence of a salcomine catalyst, the improvement which comprises employing as said inert solvent a polar solvent having a dipole moment of at least 2.7.

2. The process of claim 1 wherein the polar solvent is selected from the group consisting of γ-butyrolactone, sulfolane, N-methylpyrrolidone, acetonitrile, benzonitrile and adiponitrile.

3. The process of claim 1 wherein the oxygen-containing gas is air.

4. The process of claim 1 wherein the reaction is carried out at a pressure of from about 5 psi to about 500 psi.

5. The process of claim 1 wherein the polar solvent is selected from the group consisting of N-methyl-pyrrolidone and dimethylformamide.

6. The process of claim 1 wherein the polar solvent has a dipole moment of at least 3.3.

7. The process of claim 6 wherein the polar solvent is selected from dimethylformamide or dimethylacetamide.

8. The process of claim 7 wherein the polar solvent is dimethylformamide.

9. The process of claim 7 wherein the polar solvent is dimethylacetamide.

10. The process of claim 7 wherein the substituents are alkyl groups of from 1 to 6 carbon atoms.

11. A process for the production of a substituted p-quinone wherein the p-quinone has at least two substituents on the ring in any two or more of the 2-, 3-, 5-, and 6-positions, said substituents selected from the group consisting of alkyl of from 1 to 6 carbon atoms, which comprises reacting a similarly substituted phenol with a molecular-oxygen containing gas in the presence of salcomine and also in the presence of a solvent which is an amide selected from the group consisting of dimethylformamide, dimethylacetamide, and N-methylpyrrolidone.

12. The process of claim 11 wherein the oxygen-containing gas is air.

13. A process as claimed in claim 11 wherein the reaction is carried out at a temperature of from room temperature to 55° C.

14. A process as claimed in claim 11 wherein the reaction is carried out at a pressure of from 5 psi to 500 psi.

15. A process as claimed in claim 11 wherein said solvent is an amide solvent selected from the group consisting of dimethylformamide, and N-methylpyrrolidone.

16. A process as claimed in claim 11 carried out in the presence of dimethylformamide.

17. The process of claim 11 wherein the solvent is dimethylacetamide.

* * * * *